United States Patent [19]

D'Alelio

[11] 3,970,727

[45] July 20, 1976

[54] HALOGENATED ESTERS OF PHOSPHORUS-CONTAINING ACIDS

[76] Inventor: Gaetano F. D'Alelio, 2011 E. Cedar St., South Bend, Ind. 46617

[22] Filed: Jan. 9, 1975

[21] Appl. No.: 539,812

Related U.S. Application Data

[60] Division of Ser. No. 383,599, July 30, 1973, Pat. No. 3,900,536, which is a continuation-in-part of Ser. No. 179,543, Sept. 10, 1971, Pat. No. 3,780,144, which is a continuation of Ser. No. 785,335, Dec. 19, 1968, abandoned.

[52] U.S. Cl. .................................. 260/932; 260/2 P
[51] Int. Cl.² .......................................... C07F 9/40
[58] Field of Search ............................ 260/932, 2 P

[56] References Cited
UNITED STATES PATENTS

| | | | |
|---|---|---|---|
| 2,888,434 | 5/1959 | Shashoua | 260/932 X |
| 3,248,457 | 4/1966 | D'Alelio | 260/932 X |
| 3,284,540 | 11/1966 | D'Alelio | 260/932 X |
| 3,900,536 | 8/1975 | D'Alelio | 260/932 X |

Primary Examiner—Richard L. Raymond
Attorney, Agent, or Firm—Walter J. Monacelli

[57] ABSTRACT

This invention deals with new phosphorus-containing esters having the formula

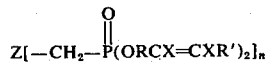

$$Z[-CH_2-\overset{O}{\underset{\|}{P}}(ORCX=CXR')_2]_n$$

wherein $n$ is an integer having a value of at least 2;
Z represents an organic moiety having a valency of $n$ and having a plurality of polymeric repeating units therein at least two of which have valencies attached to said $-CH_2P(O)(ORCX=CXR')_2$ groups of the above formula;
R represents a divalent hydrocarbon radical containing 1–20 carbon atoms;
R' represents X, hydrogen or R'';
R'' represents a monovalent hydrocarbon radical containing 1–20 carbon atoms; and
X represents chlorine or bromine. These new esters are useful particularly as fire retardants, agricultural chemicals, fuel additives, plasticizers, monomers and intermediates for the synthesis of other useful derivatives.

9 Claims, No Drawings

HALOGENATED ESTERS OF PHOSPHORUS-CONTAINING ACIDS

This application is a division of co-pending application Ser. No. 383,599, filed July 30, 1973, now U.S. Pat. No. 3,900,536, which is a continuation-in-part of copending application Ser. No. 179,543, filed Sept. 10, 1971, Pat. No. 3,780,144, which in turn is a continuation of application Ser. No. 785,335, filed Dec. 19, 1968, now abandoned.

BACKGROUND OF THE INVENTION

1. Field of the Invention

This invention involves new esters containing both phosphorus and halogen atoms in their structures. More specifically, it concerns the phosphonium esters of halogenated acetylenic alcohols.

2. Related Prior Art

No pertinent prior art is known.

STATEMENT OF THE INVENTION

The esters of this invention are represented by the formula:

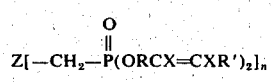

wherein $n$ is an integer having a value of at least 2;

Z represents an organic moiety having a valency of $n$ and having a plurality of polymeric repeating units therein at least two of which have valencies attached to said $-CH_2P(O)$ $(ORCX=CXR')_2$ groups of the above formula;

R represents a divalent hydrocarbon radical containing 1–20 carbon atoms;

R' represents X, hydrogen or R'';

R'' represents a monovalent hydrocarbon radical containing 1–20 carbon atoms; and X represents chlorine or bromine.

The esters of this invention are prepared readily by the following reaction using one mole of phosphite reagent per $-CH_2X$ group to be reacted:

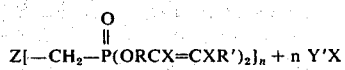

wherein Y' represents H or $-RCX=CXR'$ with the byproduct Y'X representing HX or XRCX=CXR' both of which may be distilled from the reaction mass leaving the desired product as the residue.

This reaction may be activated by the presence of a small amount of a peroxy compound such as benzoyl peroxide. However this may not be desirable when an easily polymerizable compound is being prepared in which case the activation may be effected thermally and advantageously in the presence of a polymerization inhibitor such as t-butyl catechol.

The divalent hydrocarbon radical represented by R in the above formulas can be aliphatic, cycloaliphatic or aromatic and can be saturated or have ethylenic or acetylenic unsaturation therein. Aliphatic radicals include aryl-substituted aliphatic radicals such as phenylethylene, phenylenedimethylene, etc.; aromatic radicals include alkyl, alkenyl and alkynyl substituted aromatic radicals such as tolylene, xylylene, ethylphenylene, vinylphenylene, propargylphenylene, etc.; and cycloaliphatic radicals include alkyl, alkenyl, alkynyl and aryl substituted cycloaliphatic radicals such as ethylcyclohexylene, vinylcyclohexylene, propargylcyclohexylene, phenylcycloheptylene, tolylcyclopentylene, etc. The simpler and smaller of these radicals are preferred for obvious reasons, but the more complicated radicals can also be used and are included in the scope of this invention.

These divalent hydrocarbon radicals are illustrated by the following typical radicals: $-CH_2-$; $-(CH_2)_2-$; $-(CH_2)_4-$; $-(CH_2)_7-$; $-(CH_2)_{12}-$; $-C(CH_3)_2-$; $-CH(CH_3)-$; $-CH(C_6H_5)-$; $-CH(C_6H_{11})-$; $-CH(C_4H_9)-$; $-CH(C_8H_{17})-$; $-CH_3CH(C_6H_5CH_3)-$; $-CH(CH_3)CH_2CH_2-$; $-CH_2CH=CHCH_2-$; $-CH_2C\equiv CCH_2-$; $-CH_2CH(CH=CH_2)-$; $-CH(C\equiv CH)CH_2-$; $-CH(CH_2C_6H_5)CH_2-$; $-CH_2C_6H_4CH_2-$; $-CH_2CH_2C_6H_4-$; $-C_6H_4-$; $-C_6H_3(CH_3)-$; $-C_{10}H_6-$; $-C_{10}H_5(C_2H_5)-$; $-C_6H_3(CH=CH_2)-$; $-C_6H_3(CH_2C\equiv CH)-$; $-C_6H_4-C_6H_4-$; $-C_6H_4(C_6H_5)-$; $-C_6H_9(CH=CH_2)-$; $-C_6H_{10}-$; $-C_5H_8-$; $-C_7H_{12}-$; $-C_6H_9(CH_3)-$; $-C_6H_9(C_6H_5)-$; $-C_7H_{11}(CH_2C\equiv CH)-$; $-CH_2C_6H_{10}CH_2-$; $-CH_2CH_2C_6H_{10}-$; $-(CH_2)_8CH=CH(CH_2)_{10}-$; and the like.

The organic moiety Z is the residue from the compound $Z(CH_2X)_r$ and having at least two polymeric repeating units. This organic moiety can represent aliphatic, cycloaliphatic, aromatic groups and also a plurality of such groups, similar or dissimilar, connected to each other directly or through linking radicals such as $-O-$, $-S-$, $-S(O)-$, $-S(O)_2-$, $-NH-$, $-NR''-$, $-C(O)-$, $-C(O)O-$, $-C(O)NH-$, $-C(O)NR''-$, etc. Such groups may have derivative groups thereon, which do not interfere with the reaction between the $Z(CH_2X)_n$ and $Y'OP(ORCX=CXR')_2$ reagents, such as $-OR''$, $-OC(O)R''$, $-C(O)OR''$, $-NR''_2$, $-NHR''$, $-SR''$, etc.

Typical divalent repeating units in the Z groups include the various types defined and illustrated above for R and additional typical groups include $-CH_2OCH_2-$, $-CH_2OCH_2CH_2-$, $-CH_2OC_6H_4-$, $-CH_2OC_6H_{10}-$, $-C_6H_4OCH_2CH_2-$, $-C_6H_{10}OCH_2CH_2-$, $-C_{10}H_6O(CH_2)_3-$, $-CH_2COOC_6H_{10}-$, $-COOC_6H_{10}-$, $-CH_2COOC_6H_4-$, $-COOC_6H_4-$, $-COOCH_2-$, $-CH_2C(O)C_6H_4-$, $-CH_2OOC-$, $-CH_2OOC_6H_4-$, $-CH_2N(CH_3)CH_2-$, $-CH_2N(CH_3)C_6H_4-$, $-C_6H_4NHCH_2-$, $-C_6H_4NHC_6H_4-$, $-CH_2N(C_2H_5)C_6H_{10}-$, $-CH_2SCH_2-$, $-CH_2S-C_6H_{10}-$, $-C_6H_4SCH_2-$, $-C_6H_4SC_6H_4-$, $-CONHCH_2-$, $-CONHC_6H_4-$, $-C_6H_4SCH_2CH_2-$, $-C_6H_4OCH_2-$, $-CH_2-S-C_6H_{10}-$, $-CH_2CH(CH_3)OC_6H_4-$, $-CH_2C\equiv CCH_2OCH_2-$, $-CH_2CH=CHCH_2OCH_2-$, and the like.

Typical polyvalent Z groups having a valency higher than two and having a plurality of polymeric repeating units therein at least two of which have valencies attached to said $-CH_2P(O)$ $(ORCX=CXR')_2$ groups are illustrated by the following typical groups:

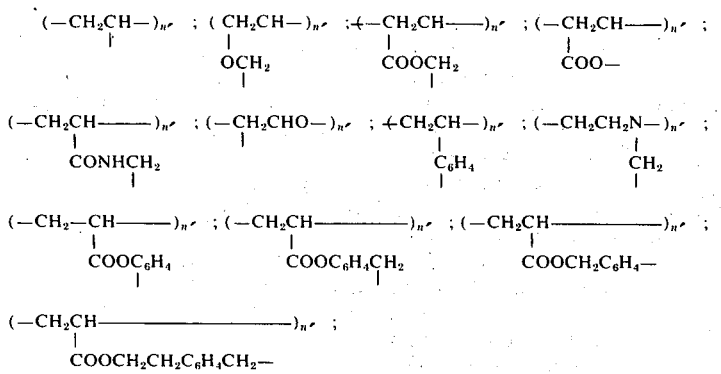

and the like. In the above formulas $n'$ is an integer advantageously of at least 3.

The above reaction for the preparation of the compounds of this invention is advantageously conducted in the temperature range of 0° to 100° C., and preferably, especially when groups are present having a strong tendency to polymerize, in the presence of a polymerization inhibitor of the various well known types, such as t-butyl catechol. When polymerization inhibitor is omitted the product may be at least partially polymerized. Preferably a polymerization inhibitor is used during the preparation of the ester so that where polymerizable groups are present which have a strong tendency to polymerize polymerization may be conducted subsequently either by itself or with copolymerizable vinyl or vinylene monomer such as styrene, alphamethyl styrene, methacrylates, acrylates maleic anhydride, unsaturated polyesters, etc., or the monomer may be used for various other purposes as indicated herein.

The period required to complete reaction varies according to the temperature used. For example at 100° C. a substantial amount of reaction is effected within 10 minutes, whereas at least 30 minutes, preferably at least one hour, is desired to effect substantial reaction at 0° C. In most cases a period of 1–5 hours is used to insure complete reaction.

Instead of using the halogenated acetylenic alcohols with the phosphorus halides as shown in the above reaction, the acetylenic alcohol may be converted first to the ester and the acetylenic ester posthalogenated to the desired product. Ester exchange reactions can also be used to prepare the esters of this invention.

The (—ORCX=CXR') type of esters of this invention differ from the esters of halogenated saturated alcohols, for example (—OCH$_2$CHXCH$_2$X), having much greater hydrolytic stability of the halogen atoms than the latter type of esters which show a much greater tendency to lose halogen. This loss of halogen occurs under conditions of high humidity, thereby limiting the utility of the saturated compound.

The novel phosphorus-containing esters of this invention are self-extinguishing when ignited and thus are particularly useful as fire-retardant additives for a host of other materials and compounds, particularly those of a resinous or polymeric nature, for example, when added to polymethyl methacrylate, polystyrene, cellulose acetate, cellulose butyrate, the polyesters, the polyurethanes, rubbers, nylon and others. They can also be used as fire-retardant impregnants for porous bodies, such as paper, wood, fiberboard, cork, etc.

As organic compounds containing phosphorus and halogen atoms they are useful also as agricultural chemicals in the fields of insecticides, herbicides, pesticides, etc., as well as gasoline additives to function as metal scavengers for anti-knock gasoline containing organo-lead, -boron or metallo-organo-compounds. Particularly are they useful as chemical intermediates in the synthesis of a host of other useful derivatives. The halo compounds can be halogenated further at the ethylenic double bond to produce higher halogenated compounds which have even greater self-extinguishing properties than the dihalo compounds. They also add to olefinic double bonds of the unsaturated compounds to yield plasticizers as well as polymerizable monomers. They react with epoxy compounds to produce substituted alcohols which can be used as modifiers of urethane polymers, polyesters, cellulose, etc.

In addition, when the compounds or derivatives contain functional groups, such as the OH groups, they can be used as modifiers in polymerization reactions or can be reacted with other functional molecules such as with the isocyanates, acid anhydrides, acid chlorides, oxirane compounds, etc., or when they contain an unsaturated olefinic group they can be homopolymerized or copolymerized with other monomers; or when they contain an amide group they can be reacted with aldehydes and polymerized alone or copolymerized with urea or melamine, or their methylol compounds can be reacted with cellulose or wool, etc.

Derivatives prepared from the compounds of this invention also find utility as flame-retardant additives and impregnants, as agricultural chemicals and as fuel additives. In addition, when the parent compounds or derivatives contain functional groups, such as the OH groups, they can be used as modifiers in polymerization reactions or can be reacted with other functional molecules such as with the isocyanates, acid anhydrides, acid chlorides, oxirane compounds, etc., or when they contain an unsaturated olefinic group they can be homopolymerized or copolymerized with other monomers; or when they contain an amide group they can be reacted with aldehydes and polymerized alone or copolymerized with urea or melamine, or their methylol compounds can be reacted with cellulose or wool, etc.

The practice of this invention is illustrated by the following examples. These examples are given merely by way of illustration and are not intended to limit the scope of the invention in any way nor the manner in which the invention can be practiced. Unless specifically indicated otherwise, parts and percentages are given as parts and percentages by weight.

EXAMPLE I

One hundred forty-five parts (145) of 1,2,3-trichloropropane are added to a solution of 106 parts of sodium carbonate dissolved in 900 parts of water and the mixture refluxed for ten hours. The water layer is then separated from the oily layer which is dried over anhydrous sodium carbonate, separated by filtration and distilled. There is obtained 115 parts of 2,3-dichloro-2-propene-1-ol, ClCH=CClCH$_2$OH, (I), b.p. 45°–46° C./1.5 mm; yield 91%.

EXAMPLE II a. To 250 parts of carbon tetrachloride is added 56 parts of propargyl alcohol (A) and to this solution there is added slowly, at room temperature, a solution of 160 parts of bromine in 250 parts of carbon tetrachloride and allowed to react at room temperature for two hours. Then the mixture is heated to 30°–40° C. for two hours. The product is distilled to recover the carbon tetrachloride and the 2,3-dibromo-2-propene-1-ol, BrCH=CBrCH OH, (II), b.p. 51°–52° C./0.7 mm; yield 93%.

b. Treatment of 1,2,3-tribromopropene with aqueous sodium carbonate by the procedure of Example 1 yields the same 2,3-dibromo-2-propene-1-ol.

EXAMPLE III

The reaction of 2-methyl-3-butyn-2-ol (B) with NaOCl under an inert atmosphere of nitrogen according to the procedure given in the Bull. soc. chim. (France) p. 1615 (1965) gives an 87% yield of 4-chloro-2-methyl-3-butyl-2-ol,

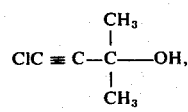

(III), b.p. 54°–56° C./18 mm. This may be halogenated by the process of Example II to give the trihalo acetylenic alcohol

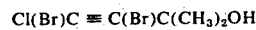

or by similarly chlorinating to give Cl$_2$C=C(Cl)C(CH$_3$)$_2$OH.

EXAMPLE IV

The reaction of 2-methyl-3-butyl-2-ol in water with Br$_2$ and NaOH by the procedure given in Ann. Chem. (Rome), 47, 118 (1957) yields 4-bromo-2-methyl-3-butyn-2-ol,

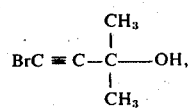

(IV), b.p. 92°–93° C./22 mm. This may be halogenated by the process of Example II to give the trihalo acetylenic alcohol

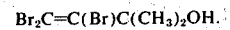

EXAMPLE V

The procedure of Example II(a) is repeated using instead of propargyl alcohol, one equivalent weight of the following acetylenic alcohols to obtain the halo-derivative corresponding to the alcohol used:

| Acetylenic Alcohol | | Dibromoethylene Derivative | |
|---|---|---|---|
| HC≡C—CH(CH$_3$)—OH | (C) | HC=C(Br)—CH(CH$_3$)—OH (Br,Br) | (V) |
| HC≡C—CH(C$_2$H$_5$)—OH | (D) | HC=C(Br)—CH(C$_2$H$_5$)—OH (Br,Br) | (VI) |
| HC≡C—CH(C$_3$H$_7$)—OH | (E) | HC=C(Br)—CH(C$_3$H$_7$)—OH (Br,Br) | (VII) |
| HC≡C—CH(C$_4$H$_9$)—OH | (F) | HC=C(Br)—CH(C$_4$H$_9$)—OH (Br,Br) | (VIII) |
| HC≡C—CH(C$_8$H$_{17}$)—OH | (G) | HC=C(Br)—CH(C$_8$H$_{17}$)—OH (Br,Br) | (IX) |
| HC≡C—CH(C$_6$H$_5$)—OH | (H) | HC=C(Br)—C(C$_6$H$_5$)—OH (Br,Br) | (X) |
| HC≡C—C(CH$_3$)(CH$_3$)—OH | (B) | HC=C(Br)—C(CH$_3$)(CH$_3$)—OH (Br,Br) | (XI) |
| HC≡C—C(CH$_3$)(C$_2$H$_5$)—OH | (I) | HC=C(Br)—C(CH$_3$)(C$_2$H$_5$)—OH (Br,Br) | (XII) |
| HC≡C—C(CH$_3$)(C$_4$H$_9$)—OH | (J) | HC=C(Br)—C(CH$_3$)(C$_4$H$_9$)—OH (Br,Br) | (XIII) |
| HC≡C—C(C$_4$H$_9$)(C$_4$H$_9$)—OH | (K) | HC=C(Br)—C(C$_4$H$_9$)(C$_4$H$_9$)—OH (Br,Br) | (XIV) |
| H$_3$C—C≡C—CH$_2$OH | (L) | CH$_3$C=C(Br)—CH$_2$OH (Br,Br) | (XV) |
| H$_3$C—C≡C—CH$_2$CH$_2$OH | (M) | CH$_3$C=C(Br)—CH$_2$CH$_2$OH (Br,Br) | (XVI) |
| C$_6$H$_5$C≡C—(CH$_2$)$_{10}$OH | (N) | C$_6$H$_5$C=C(Br)—(CH$_2$)$_{10}$OH (Br,Br) | (XVII) |
| H$_{41}$C$_{20}$C≡C—CH$_2$OH | (O) | H$_{41}$C$_{20}$C=C(Br)—CH$_2$OH (Br,Br) | (XVIII) |
| H$_3$CC≡C—CH$_2$·CH(CH$_3$)—OH | (P) | H$_3$CC=C(Br)—CH$_2$CH(CH$_3$)—OH (Br,Br) | (XIX) |
| C$_4$H$_9$C≡C—CH$_2$OH | (Q) | H$_9$C$_4$C=C(Br)—CH$_2$OH (Br,Br) | (XX) |
| C$_6$H$_5$C≡C—CH$_2$OH | (R) | C$_6$H$_5$C=C(Br)—CH$_2$OH (Br,Br) | (XXI) |
| C$_6$H$_5$C≡C—CH$_2$CH$_2$OH | (S) | C$_6$H$_5$C=C(Br)—CH$_2$CH$_2$OH (Br,Br) | (XXII) |
| C$_6$H$_{11}$C≡C—CH$_2$OH | (T) | C$_6$H$_{11}$C=C(Br)—CH$_2$OH (Br,Br) | (XXIII) |
| C$_6$H$_5$C≡C—CH(CH$_3$)—OH | (U) | C$_6$H$_5$C=C(Br)—CH(CH$_3$)—OH (Br,Br,CH$_3$) | (XXIV) |

-continued

| Acetylenic Alcohol | | Dibromoethylene Derivative | |
|---|---|---|---|
| $C_6H_5C \equiv C-\underset{\underset{CH_3}{\mid}}{\overset{CH_3}{\overset{\mid}{C}}}-OH$ | (V) | $C_6H_5C=\underset{\underset{CH_3}{\mid}}{\overset{Br\ Br\ CH_3}{\overset{\mid\ \mid\ \mid}{C-C}}}-OH$ | (XXV) |
| $ClC \equiv C-\underset{\underset{CH_3}{\mid}}{\overset{CH_3}{\overset{\mid}{C}}}-OH$ | (III) | $ClC=\underset{\underset{CH_3}{\mid}}{\overset{Br\ Br\ CH_3}{\overset{\mid\ \mid\ \mid}{C-C}}}-OH$ | (XXVI) |
| $BrC \equiv C-\underset{\underset{CH_3}{\mid}}{\overset{CH_3}{\overset{\mid}{C}}}-OH$ | (IV) | $BrC=\underset{\underset{CH_3}{\mid}}{\overset{Br\ Br\ CH_3}{\overset{\mid\ \mid\ \mid}{C-C}}}-OH$ | (XXVII) |
| $C_{10}H_7C \equiv CCH_2OH$ | (W) | $C_{10}H_7C=\overset{Br\ Br}{\overset{\mid\ \mid}{C}}-CH_2OH$ | (XXVIII) |

EXAMPLE VI a. To a solution of 56 parts of propargyl alcohol and 0.1 part of iodine in 300 parts of tetrachloroethylene is slowly passed chlorine gas while exposed to an ultraviolet lamp until 70 parts of chlorine are reacted. The halogenated product is then recovered by distillation and the majority of the product is identical to the 2,3-dichloro-2-propene-1-ol of Example I.

b. In a similar manner there is prepared

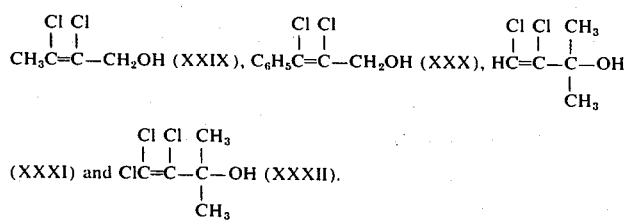

$CH_3C=\overset{Cl\ Cl}{\overset{\mid\ \mid}{C}}-CH_2OH$ (XXIX), $C_6H_5C=\overset{Cl\ Cl}{\overset{\mid\ \mid}{C}}-CH_2OH$ (XXX), $HC=\underset{\underset{CH_3}{\mid}}{\overset{Cl\ Cl\ CH_3}{\overset{\mid\ \mid\ \mid}{C-C}}}-OH$ (XXXI) and $ClC=\underset{\underset{CH_3}{\mid}}{\overset{Cl\ Cl\ CH_3}{\overset{\mid\ \mid\ \mid}{C-C}}}-OH$ (XXXII).

The halogenated acetylenic alcohols prepared in the above examples may be used in preparing the P(ORCX=CXR')$_3$ and HOP(ORCX=CXR')$_2$ reagents used for preparing the new compositions of this invention as illustrated in some of the following examples.

EXAMPLE VII a. The phosphite ester,

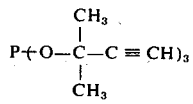

$P(\!+\!O-\underset{\underset{CH_3}{\mid}}{\overset{CH_3}{\overset{\mid}{C}}}-C \equiv CH)_3$ is prepared from PCl$_3$ and $HC \equiv C-\underset{\underset{CH_3}{\mid}}{\overset{CH_3}{\overset{\mid}{C}}}-OH$ (B)

by the procedure given in U.S. Pat. 2,278,791, Dec. 27, 1955, and converted by the procedure of Example II(a) by reaction with Br$_2$ to

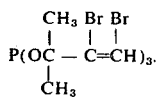

$P(O\underset{\underset{CH_3}{\mid}}{\overset{CH_3\ Br\ Br}{\overset{\mid\ \mid\ \mid}{C-C=CH}}})_3$.

b. In a manner similar to the procedure of VII(a) the acetylenic alcohols III, IV, C, D, L and M are converted to the phosphite esters, P$\!+\!$ORC $\equiv$ CR'')$_3$, and by post bromination to esters corresponding to the formula

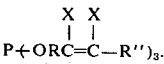

$P\!+\!ORC=\overset{X\ X}{\overset{\mid\ \mid}{C}}-R'')_3.$

EXAMPLE VIII

A mixture of 46 parts of PCl$_3$, 126 parts of 2,3-dichloro-2-propene-1-ol and 150 parts of toluene is refluxed until no more HCl is evolved from the reaction. The mixture is then allowed to cool to room temperature; then 5 parts of anhydrous sodium carbonate and 3 parts of decolorizing carbon are added to the solution and allowed to stand with stirring for 8 to 24 hours. The solution is then filtered and the filtrate distilled at 0.5 to 14 mm Hg pressure to recover the toluene. The yield of almost colorless residue is 96% of the theoretical amount. The infrared spectra of the product confirm the absence of the band for the —OH group of the alcohol and the presence of the band for the ester group. The product is a viscous oil insoluble in water but soluble in benzene and toluene. The elemental analysis of the product: percent C, 26.95; percent H, 2.24; percent Cl, 52.56; are in close agreement with the theoretical values of C, 26.42; H, 2.20; cl, 52.02 for P(OCH$_2$CCl=CHCL)$_3$. The boiling point of the product is higher than 120° C. at 0.5 mm Hg. Attempts to distill the product at higher pressure results in secondary reactions which change the nature of the product, which product, however, is still self-extinguishing. Other triesters of this type having other R groups in place of the —CH$_2$— and/or having bromine in place of the chlorine or having the tetrachloro or tetrabromo structure can be similarly prepared for use as intermediates in preparing phosphate esters of the present invention.

EXAMPLE IX

A mixture of 10.15 parts of P(OCH$_2$CCl=CHCl)$_3$ and 15 parts of CH$_3$COOH are heated at 100° C. for two hours following which it is distilled at 15 mm pressure to recover 42 parts of CH$_3$COOCH$_2$CCl=CHCl, leaving as a residue 86.2 parts of HOP(OCH$_2$CCl=CHCl)$_2$ which on analysis is shown to contain 46.4% of Cl compared to a theoretical value of 47.3.

Various other di and trihalogenated acetylenic alcohols can be used to prepare various HOP(ORCX=CX-R')$_2$ reagents suitable for use in the practice of this invention. By using other acids in place of the acetic acid, for example acrylic acid, more valuable byproducts such as $CH_2=CHCOOCH_2Cl=CHCl$ may be obtained.

EXAMPLE X

A mixture of 40.6 parts of $P(OCH_2CCl=CHCl)_3$ and 8.2 parts of $P(OH)_3$ are heated at 75° C. for three hours and there is obtained the viscous product comprising as the major product 48.8 parts of $HOP(OCH_2CCl=CHCl)_2$.

By substituting various other $P(ORCX=CXR')_3$ compounds for the $P(OCH_2CCl=CHCl)_3$, other $HOP(ORCX=CXR')_2$ reagents useful in the practice of this invention may be prepared.

EXAMPLE XI a. An equimolar mixture of $P(OCH_2CCl=CHCl)_3$ and $CH_2=C(CH_3)COOCH_2Cl$ is heated at 100° C. for 3 hours in the presence of 0.5% t-butyl catechol following which the mixture is distilled to remove $ClCH=CClCH_2Cl$ leaving as a residue the ester $CH_2=C(CH_3)—COOCH_2P(O)(OCH_2CCl=CHCl)_2$.
The above product is verified by C, H, P, Cl and O analyses.

b. The procedure of (a) is repeated using an equivalent amount of $CH_2=C(Cl)COOCH_2Cl$ in place of the $CH_2=C(CH_3)COOCH_2Cl$ to produce the ester of the formula $CH_2=C(Cl)COOCH_2P(O)(OCH_2CCl=CHCl)_2$.

c. The procedure of (a) is repeated using equivalent amounts of $CH_2=CHCOOCH_2Cl$ and $P(OCH_2CBr=CHBr)_3$ to give the ester having the formula $CH_2=CHCOOCH_2P(O)OCH_2CBr=CHBr)_2$ d. The procedure of (a) is repeated using equivalent amounts of $CH_2=CHCOOCH_2Cl$ and $P(OCH_2CCl=CCl_2)_2$ to give the ester having the formula $CH_2=CHCOOCH_2P(O)OCH_2CCl=CCl_2)_2$ e. The procedure of (a) is repeated using equivalent amounts of $CH_2=C(CH_2)COOCH_2Br$ and $P(OCH_2CCl=CCl_2)_3$ to give the ester having the forumla $CH_2=C(CH_3)COOCH_2P(O)(OCH_2CCl=CCl_2)_2$ f. The procedure of (a) is repeated using equivalent amounts of $CH_2=C(CH_3)COOCH_2Cl$ and $P[OC(CH_3)_2CBr=CHBr]_3$ to give the ester having the formula $CH_2=C(CH_3)COOCH_2P(O)-[OC(CH_3)_2CBr=CHBr]_2$ g. The procedure of (a) is repeated using equivalent amounts of $CH_2=CHCOO(CH_2)_2Cl$ and $P(OCH_2CCl=CHCl)_3$ to give the ester of the formula $CH_2=CHCOO(CH_2)_2P(O)(OCH_2CCl=CHCl)_2$ h. The procedure of (a) is repeated using equivalent amounts of $CH_2=CHCOO(CH_2)_4Cl$ and $HOP(OCH_2CCl=CHCl)_2$ to give the ester having the formula $CH_2=CHCOOCH_2P(O)(OCH_2CCl=CHCl)_2$ The procedure of (a) is repeated a number of times using equivalent amounts of appropriate starting materials as illustrated above to produce esters having the following formulas:

i. $CH_2=CHCOOCH_2C_6H_4CH_2P(O)-[O(CH_2)_4CCl=CHCl]_2$ j. $CH_2=CHCOOC_6H_{10}CH_2P(O)-(OC_6H_{10}CCl=CHCl)_2$ k. $CH_2=CHCOOC_6H_4CH_2P(O)-(OC_6H_4CCl=CHCl)_2$ l. $CH_2=CHCOOC_6H_4CH_2CH_2P(O)-(OCH_2C_6H_4CCl=CHCl)_2$ m. $CH_2=CHCOOCH_2CH_2(PO)(OCH_2CBr=CHBr)_2$

The compounds prepared in Example XI are also disclosed in copending application Ser. No. 383,583 filed the same date herewith, now Pat. No.. 3,886,236. However while they are covered generically in that application they are covered specifically only in the claims of this application.

EXAMPLE XII a. To 47.8 parts of $HOP(OCH_2CBr=CHBr)_2$ in 150 parts of toluene under a nitrogen atmosphere, there is added slowly at 20°–30° C. a solution containing 100 parts of toluene, 13.5 parts of $CH_2=CHCOOCH_2CH_2Cl$, 0.5 parts of tertiary butyl catechol and 5.9 parts of trimethyl amine, and the mixture stirred for 3 hours. The precipitated amine hydrochloride $(CH_3)_3N.HCl$ is removed by filtration, and the filtrate containing the product $CH_2=CHCOOCH_2CH_2P(O)(OCH_2CBr=CHBr)_2$ is washed with distilled water until the washings are neutral. The toluene solution containing the polymerizable monomer, $CH_2=CHCOOCH_2CH_2P(O)(OCH_2CBr=CHBr)_2$, can be used as prepared for the preparation of polymers and copolymers, or grafted to cellulose fibers, or the toluene can be removed by distillation at reduced pressures leaving an almost quantitative yield of the monomer.

The procedure of (a) is repeated a number of times using equivalent amounts of the reagents and obtaining the products indicated in the table below.

| | Reagents | Product |
|---|---|---|
| (b) | $HOP(OCH_2CCl=CHCl)_2$ + $CH_2=CHCOOCH_2CH_2Cl$ | $CH_2=CHCOOCH_2CH_2P(O)—(OCH_2CCl=CHCl)_2$ |
| (c) | $HOP(OCH_2CCl=CHCl)_2$ + $CH_2=C(CH_3)COOCH_2CH_2Cl$ | $CH_2=C(CH_3)COOCH_2CH_2P(O)—(OCH_2CCl=CHCl)_2$ |

| Reagents | Product |
|---|---|
| (d) HOP(OCH$_2$CCl=CHCl)$_2$ + CH$_2$=C(Cl)COOCH$_2$CH$_2$Br | CH$_2$=C(Cl)COOCH$_2$CH$_2$P(O)— (OCH$_2$CCl=CHCl)$_2$ |
| (e) HOP[O(CH$_2$)$_3$CCl=CHCl]$_2$ + CH$_2$=C(Cl)COOCH(CH$_3$)CH$_2$Cl | CH$_2$=C(Cl)COOCH(CH$_3$)CH$_2$P(O)— [O(CH$_2$)$_3$CCl=CHCl]$_2$ |
| (f) HOP(OCH$_2$CCl=CCl$_2$)$_2$ + CH$_2$=C(Cl)COOCH$_2$C$_6$H$_4$CH$_2$Br | CH$_2$=C(Cl)COOCH$_2$C$_6$H$_4$CH$_2$P(O)— (OCH$_2$CCl=CCl$_2$)$_2$ |
| (g) HOP(OC$_6$H$_4$CCl=CHCl)$_2$ + CH$_2$=C(CH$_3$)COOC$_6$H$_{10}$CH$_2$Cl | CH$_2$=C(CH$_3$)COOC$_6$H$_{10}$CH$_2$P(O)— (OC$_6$H$_4$CCl=CHCl)$_2$ |
| (h) HOP(OCH$_2$CBr=CBr$_2$)$_2$ + CH$_2$=CHCOO(CH$_2$)$_3$Cl | CH$_2$=CHCOO(CH$_2$)$_3$P(O)— (OCH$_2$CBr=CBr$_2$)$_2$ |
| (i) HOP(OCH$_2$CCl=CHCl)$_2$ + CH$_2$=CHOOCCH$_2$Cl | CH$_2$=CHOOCCH$_2$P(O)— (OCH$_2$CCl=CHCl)$_2$ |
| (j) HOP(OCH$_2$CBr=CHBr)$_2$ + ClCH=CClCH$_2$Cl | ClCH=CClCH$_2$P(O)— (OCH$_2$CBr=CHBr)$_2$ |
| (k) HOP(OCH$_2$CCl=CHCl)$_2$ + CH$_2$—CH=CH$_2$Cl \O/ | CH$_2$—CHCH$_2$P(O)— \O/ (OCH$_2$CCl=CHCl)$_2$ |
| (l) HOP(OCH$_2$CCl=CHCl)$_2$ + CH$_2$—CH—CH$_2$Cl  \| \| OH OH | CH$_2$—CHCH$_2$P(O)— \| \| OH OH (OCH$_2$CCl=CHCl)$_2$ |

EXAMPLE XIII

Samples of the various phosphorus esters of Examples XI and XII are placed individually in a microcrucible and in each case the contents ignited by the flame of a microburner. When the flame is withdrawn, in each case burning stops completely.

EXAMPLE XIV

A mixture of 50 parts of methyl methacrylate, 5 parts of

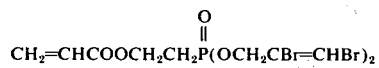

and 0.5 parts of benzoyl peroxide is polymerized in a sealed container under nitrogen at 80°C. until a hard polymer is obtained, which is self-extinguishing. Similar self-extinguishing polymers are obtained when, instead of

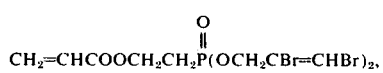

the individual esters of Examples XI and XII are used.

EXAMPLE XV

The procedure of Example XIV is repeated using instead of methyl methacrylate, the monomers styrene, acrylonitrile and vinyl acetate respectively, and self-extinguishing polymers are obtained in each case.

EXAMPLE XVI

Ten parts of

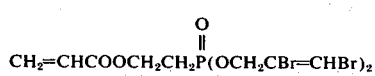

are added respectively to each of the following, which are approximately 50% solvents and 50% solids, (a) a clear alkyd varnish, (b) a cellulose acetate-butyrate lacquer, (c) a white-pigment oil-modified epoxy paint, and (c) a pigmented urethane-type paint; then films are cast from the mixtures and allowed to dry or cure for four days. Attempts to ignite the resulting films showed in each case that they are self-extinguishing. Similar results are obtained when the other esters selected from Examples XI and XII are similarly tested.

EXAMPLE XVII

A skein of 20 parts of cotton thread is placed in 500 parts of an aqueous solution containing 2.5 parts NaOH, 2.5 parts CS$_2$ and 0.05 parts of sodium dodecylbenzene sulfonate and allowed to stand for 30 minutes. The thread is then removed, washed thoroughly with distilled water, and immersed in 500 parts of a solution containing 0.05 parts of FeSO$_4$.(NH$_4$)$_2$SO$_4$ and 1.5 parts of tetra-bis-hydroxymethyl phosphonium chloride for 10 minutes. The thread is then washed with distilled water and suspended in 1000 parts of an emulsion containing 8 parts of $CH_2=CHCOOCH_2CH_2P(O)(OCH_2CBr=CHBr)_2$, 0.1 parts of sodium dodecylbenzene sulfonate and 1.5 parts of hydrogen peroxide and the mixture heated with agitation under nitrogen for 3 hours. The thread is then removed, washed with water and dried. There is obtained 28 parts of grafted thread, which when suspended and its end ignited, is self-extinguishing when the source of the flame is withdrawn.

EXAMPLE XVIII

A mixture of 50 parts

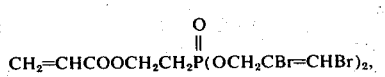

50 parts of toluene and 0.5 parts of benzoyl peroxide is polymerized in a sealed container under nitrogen and at 80°C. for 10 hours. The toluene is evaporated to give a solid resin. Five parts of this is mixed with 100 parts respectively of polystyrene, polymethyl methacrylate, polyacrylonitrile, polybutadiene, polyvinyl-acetate and molded in each case to a hard casting. In each case attempts to ignite each casting showed the product to be self-extinguishing in each case. The procedure is repeated with each of the other monomers of Examples XI and XII and in each case the product is found to be self-extinguishing.

As shown above the phosphorus-containing esters of this invention having acrylic groups therein are polymerizable by themselves or in mixtures with each other or in mixtures with other vinyl or vinylidene monomers, sometimes referred to herein as vinyl monomers, such as styrenes, i.e., styrene, alphamethylstyrene, vinyl naphthalene, vinyl diphenyl, etc., with acrylates, such as methyl acrylate, methyl methacrylate, butyl acrylate, ethyl chloracrylate, etc., vinyl esters such as vinyl acetate, vinyl benzoate, vinyl butyrate, etc., acrylonitrile, methacrylonitrile, esters of polymerizable dibasic acids such as dimethyl maleate, diethyl fumarate, diallyl phthalate, divinyl azelate, dimethyl itaconate, etc., maleic anhydride, itaconic anhydride, etc.

In producing self-extinguishing copolymers with such copolymerizing monomers, such properties are exhibited with as little as 0.1 percent by weight, preferably at least 1 percent by weight, of a monomer of this invention. In blends of homopolymers or copolymers of these phosphorus-containing esters with other polymers, such as polystyrene, etc., there is advantageously at least 0.1 percent, preferably at least 1 percent by weight, of the product represented by the phosphorus-containing ester portion.

In polymerizing such acrylic esters of this invention the various polymerization systems and techniques known in the art may be used, such as free-radical, e.g. peroxy and azo systems thermal, radiation and various other systems. For most purposes for which the polymer products are to be used molecular weights of at least 500, preferably at least 1,000, are desirable.

As indicated above and where it may be desired, these polymers can be produced directly with the preparation of the ester by omitting the inhibitor and allowing polymerization to occur simultaneously. If the polymerization has not progressed sufficiently by the time the preparation reaction is completed, heating may be continued at the same or higher temperatures, or catalysts, such as benzoyl peroxide, etc. may be added to complete the polymerization.

While such acrylic esters or monomers of this invention have been represented by various formulas, they may also be represented generically by the formula

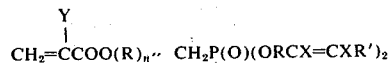

wherein $n''$ represents an integer having a value of 0 or 1 and the other symbols have the definitions given above.

Similarly the repeating units in polymers produced from these esters can be represented by the formula

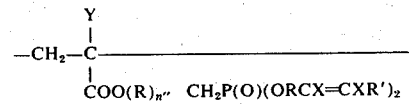

Polymers having repeating units similar to those produced by polymerizing the monomer esters of this invention may also be produced by polymerizing an acrylate portion of the monomer, such as a (chloroalkyl)acrylate and reacting the remainder of the ester monomer repeating unit by reactions similar to those used in preparing the monomer. For example, poly(beta-chlorethyl)acrylate may be dissolved or suspended in toluene, etc., and then reacted with an appropriate amount of $HOP(ORCX=CXR')_2$ or $P(ORCX=CXR')_3$ to give repeating units having the formula

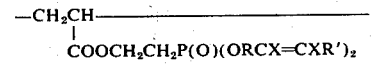

When copolymers of the polymerizable monomers of this invention are prepared with styrene, methyl methacrylate, vinyl acetate, acrylonitrile, etc. as comonomers, the fire retardant effect is noted when as little as 0.1% of the halogenated monomer is present and preferably at least 1% by weight is used.

Other polymerizable compounds are also prepared by the process of Examples XI and XII using in place of the acrylic starting esters of those examples and without the polymerization inhibitor where appropriate, various other $-CH_2X$ containing polymers having the formula $Z(CH_2X)_n$.

EXAMPLE XIX

A mixture of one mole of $P(OCH_2CCl=CHCl)_3$ and one mole of $CH_2=CHCH_2Cl$ are heated at 100°C. for 3 hours, following which the mixture is distilled to recover $ClCH=CClCH_2Cl$, leaving as a residue, the product

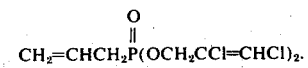

The analyses for C, H, P, O and Cl confirm the identity of this structure.

EXAMPLE XX

One mole of $P(OCH_2CCl=CHCl)_3$ and one mole of each of $CH_2=CHCH_2Br$ and $ClCH_2COOCH_2CH=CH_2$ are reacted separately by the procedure of Example XIX, and there are obtained $CH_2=CHCH_2P(O)-(OCH_2CCl=CHCl)_2$, $H_2C=HCCH_2OOCCH_2P(O)-(OCH_2CCl=CHCl)_2$, respectively.

EXAMPLE XXI

The procedure of Example XX is repeated using each time an equivalent amount of $P(OCH_2CBr=CHBr)_3$ and there are obtained:

$CH_2=CHCH_2P(O)(OCH_2CBr=CHBr)_2$ $CH_2=CHCH_2OOCCH_2 2CBr=CHBr)_2$

EXAMPLE XXII a. To a toluene solution containing one mole of $HOP-(OCH_2CBr=CHBr)_2$ there is slowly added, at 20°–30° C. and under a nitrogen atmosphere, a toluene solution containing one mole of $CH_2=C(CH_3)CH_2Br$ and one mole of trimethylamine. After the mixture is stirred for 3 hours, the precipitated amine hydrohalide is removed by filtration, and the filtrate containing the product $CH_2=(CH_3)CH_2P(O)(OCH_2CBr=CHBr)_2$ is washed with distilled water until the washings are neutral. Removal of the toluene by distillation under reduced pressure leaves practically a quantitative yield of the product whose identity is confirmed by C, H, P, O and Br analyses.

The above procedure is repeated a number of times using each time, in place of the one mole of methallyl bromide, one half mole respectively of a variety of $-CH_2X$ containing compounds as indicated below to produce the corresponding compounds also as indicated.

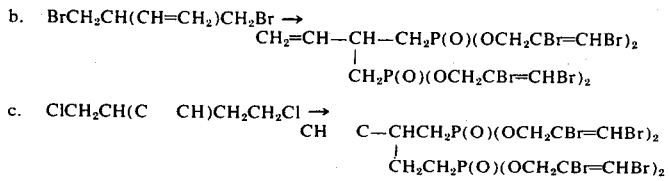

When the above procedure is repeated in each case using $HOP(OCH_2CCl=CHCl)_2$ as the phosphorus-containing reagent the corresponding chlorinated products are obtained. These same compounds may be prepared by starting with $P(OCH_2CSr=CHBr)_2$ (and the corresponding chlorine derivative) and using the procedure of Example XIX.

EXAMPLE XXIII

The procedure of Example XXII is repeated a number of times, using one mole of $HOP-(OCH_2CBr=CHBr)_2$ and one mole of $(CH_3)_3H$ for each equivalent of $-CH_2X$ in the respective compounds, and using the following polyvalent compositions with production of the indicated products:

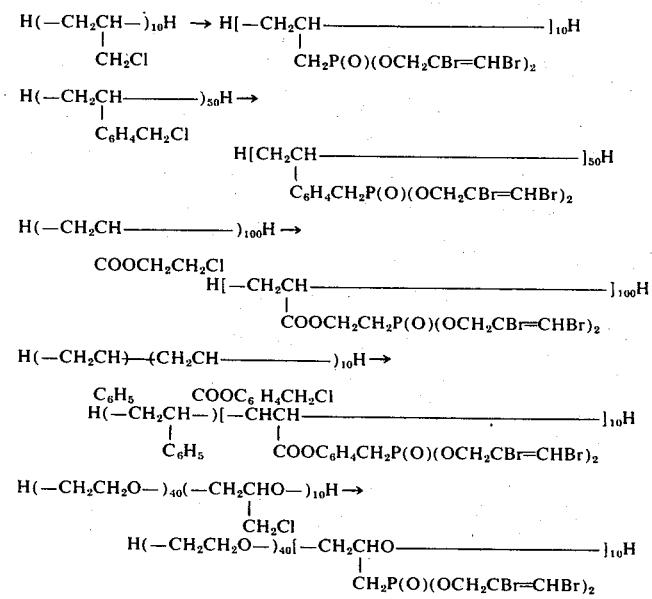

When the procedures of Example XXIII are repeated using equivalent amounts of $HOP(OCH_2CCl=CHCl)_2$ the corresponding chlorinated products are obtained.

EXAMPLE XXIV

The procedures of Examples XIX and XXI are repeated a number of times using, in place of the respective phosphorus dihaloacetylenic compounds a variety of halogenated compounds as indicated below with the product in each case containing the corresponding phosphorus halogenated acetylenic groups therein:

a. $P(OCH_2CBr=CBr_2)_3$ b. $P(OCH_2CCl=CCl_2)_3$ c. $P(OCH_2CH_2CBr=CBr_2)_3$ d. P[O(CH$_2$)$_4$CCl=CCl$_2$]$_3$ e. P[O(CH$_2$)$_3$CBr=CHBr]$_3$ f. P[O(CH$_2$)$_4$CCl=CHCl]$_3$ g. P(OCH$_2$CBr=CBrCH$_3$)$_3$ h. P(OCH$_2$CCl=CClC$_6$H$_5$)$_3$ i. P(OCH$_2$CCl=CClC$_6$H$_{11}$)$_3$ j. P(OC$_6$H$_4$CCl=CHCl)$_3$ k. P(OC$_6$H$_{10}$CBr=CHBr)$_3$ l. P[OCH$_2$CCl=CCl(CH$_2$)$_4$CH$_3$]$_3$

EXAMPLE XXV

The procedures of Examples XXII and XXIII are repeated a number of times using in place of the hydroxy phosphorus dihaloacetylenic compounds a variety of halogenated compounds as indicated below with the product in each case containing the corresponding phosphorus halogenated acetylenic groups therein:

a. HOP(OCH$_2$CBr=CBr$_2$)$_2$ b. HOP(OCH$_2$CCl=CCl$_2$)$_2$ c. HOP[OCH(C$_6$H$_5$)CCl=CHCl]$_2$ d. HOP[OCH(C$_6$H$_{11}$)CCl=CHCl]$_2$ e. HOP[OCH(C$_4$H$_9$)CH$_2$CCl=CHCl]$_2$ f. HOP[OC$_6$H$_4$CCl=CHCl]$_2$ g. HOP[OC$_6$H$_4$C$_6$H$_4$CBr=CHBr]$_2$ h. HOP(OCH$_2$C$_6$H$_4$CH$_2$CCl=CHCl)$_2$ i. HOP(OCH$_2$CCl=CClC$_6$H$_5$)$_2$ j. HOP(OCH$_2$CCl=CClCh$_3$)$_2$ k. HOP(OCH$_2$CBr=CBrC$_6$H$_{11}$)$_2$ l. HOP(OCH$_2$CBr=CBrC$_4$H$_9$)$_2$

EXAMPLE XXVI

Samples of each of the various phosphorus esters of Examples XIX through XXV are placed individually in a microcrucible and in each case the contents ignited by the flame of a microburner. When the flame is withdrawn, burning stops completely in each case. When tested in various compositions as in Example XVI the various esters of these examples show similar fire retardant properties. These effects are noted with as little as 0.1%, preferable at least 1% of the phosphorus halide ester.

EXAMPLE XXVII

An equimolar mixture of vinylbenzyl chloride, CH$_2$=CHC$_6$H$_4$CH$_2$Cl, and P(OCH$_2$CCl=CHCl)$_3$ is reacted by the procedure of Example XI(a) leaving as a residue CH$_2$=CHC$_6$H$_4$CH$_2$P(O)(OCH$_2$CCl=CHCl)$_2$ as a viscous oil whose elemental analyses for P and Cl are in good agreement with the calculated values for the compound. Polymerization of this monomer by the procedure of Example XIV yields a self-extinguishing polymer having the repeating unit —CH$_2$CH—
|
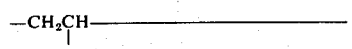
C$_6$H$_4$CH$_2$P(O)(OCH$_2$CCl=CHCl)$_2$ The corresponding bromo derivatives are prepared and polymerized in the same manner and with similar results.

While certain features of this invention have been described in detail with respect to the various embodiments thereof, it will, of course, be apparent that other modifications may be made within the spirit and scope of this invention, and it is not intended to limit the invention to the exact details shown above except insofar as they are defined in the following claims.

The invention claimed is:

1. A phosphorus-halogen-containing polymer having at least five repeating units of the formula

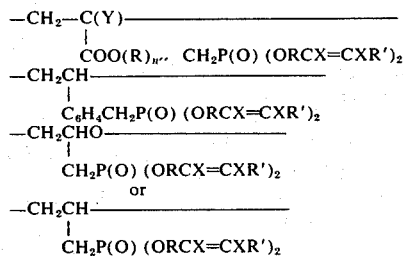

wherein Y represents H, CH$_3$ or Cl;
X represents Cl or Br;
R represents a divalent hydrocarbon radical of 1–20 carbon atoms;
R' represents H, X or R";
R" represents a monovalent hydrocarbon radical of 1–20 carbon atoms and
n" represents an integer having a value of 0 or 1.

2. The polymer of claim 1 which contains a plurality of repeating units having the formula

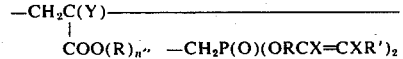

3. The polymer of claim 1 which contains a plurality of repeating units having the formula

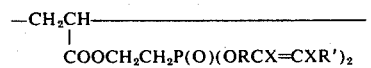

4. The polymer of claim 1 which contains a plurality of repeating units having the formula

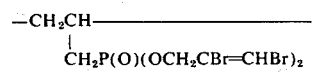

5. The polymer of claim 1 which contains a plurality of repeating units having the formula

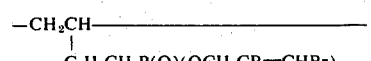

6. The polymer of claim 1 which contains a plurality of repeating units having the formula

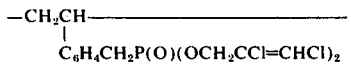
7. The polymer of claim 1 which contains a plurality of repeating units having the formula
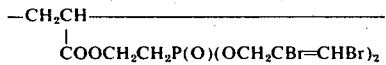
8. The polymer of claim 1 which contains a plurality of repeating units having the formula
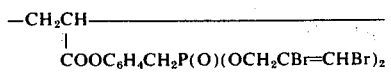
9. The polymer of claim 1 which contains a plurality of repeating units having the formula
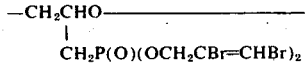
* * * * *

UNITED STATES PATENT OFFICE
CERTIFICATE OF CORRECTION

Patent No. 3,970,727           Dated July 20, 1976

Inventor(s) Gaetano F. D'Alelio

It is certified that error appears in the above-identified patent and that said Letters Patent are hereby corrected as shown below:

Col. 15, line 21, correct the formula to read:
$CH_2=CHCH_2OOCCH_2P(O)(OCH_2CBr=CHBr)_2$;

Col. 15, line 57, correct the formula to read:
$CH_2=C(CH_3)CH_2P(O)(OCH_2CBr=CHBr)_2$;

Col. 16, lines 7-12, correct the reaction "c" and formulas therein by inserting triple bonds in the blank spaces so that (C CH) will read (C≡CH) and CH C- will read CH≡C- ;

Col. 16, line 17, correct the formula to read:
$P(OCH_2CBr=CHBr)_2$;

Col. 16, line 23, correct $(CH_3)_3H$ to read $(CH_3)_3N$;

Col. 16, in Example XXIII, in the second last reaction the reactant should have a vertical bond inserted in two places so that the formula will read:

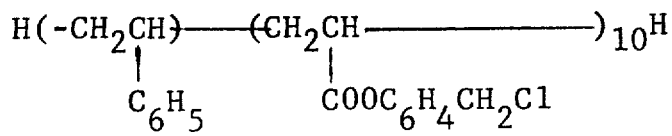

Col. 18, line 38, correct 0or1 to read 0 or 1.

Signed and Sealed this

Fifth Day of October 1976

[SEAL]

Attest:

RUTH C. MASON  
*Attesting Officer*

C. MARSHALL DANN  
*Commissioner of Patents and Trademarks*